(12) United States Patent
Miyauchi

(10) Patent No.: US 8,425,952 B2
(45) Date of Patent: Apr. 23, 2013

(54) METHOD FOR TREATING PROSTATE CANCER

(76) Inventor: Yutaka Miyauchi, Cary, NC (US)

( * ) Notice: Subject to any disclaimer, the term of this patent is extended or adjusted under 35 U.S.C. 154(b) by 0 days.

(21) Appl. No.: 13/388,299

(22) PCT Filed: Aug. 20, 2011

(86) PCT No.: PCT/US2011/048532
§ 371 (c)(1),
(2), (4) Date: Jan. 31, 2012

(87) PCT Pub. No.: WO2012/154192
PCT Pub. Date: Nov. 15, 2012

(65) Prior Publication Data
US 2013/0045288 A1 Feb. 21, 2013

(51) Int. Cl.
*A61K 36/752* (2006.01)
*A61K 36/886* (2006.01)
*A61K 36/00* (2006.01)

(52) U.S. Cl.
USPC ............................ 424/736; 424/725; 424/744

(58) Field of Classification Search ....................... None
See application file for complete search history.

*Primary Examiner* — Qiuwen Mi
(74) *Attorney, Agent, or Firm* — Jules E. Goldberg

(57) ABSTRACT

A method for treatment of a human subject with prostate cancer is disclosed. The method comprises administering an anti-prostate cancer effective amount of a composition obtained by the extraction of fresh citrus fruit peels in sake.

18 Claims, 6 Drawing Sheets

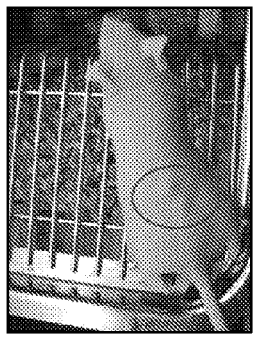 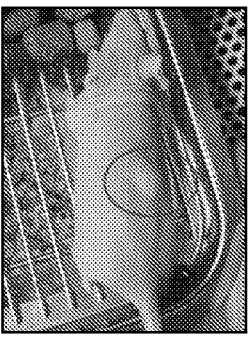 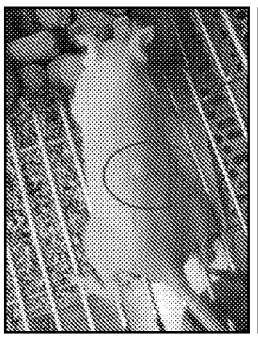 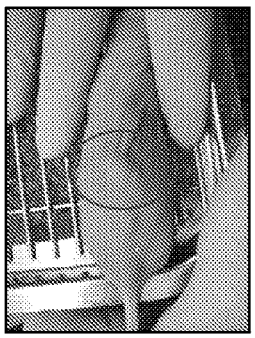
FIG. 6A   FIG. 6B   FIG. 6C   FIG. 6D
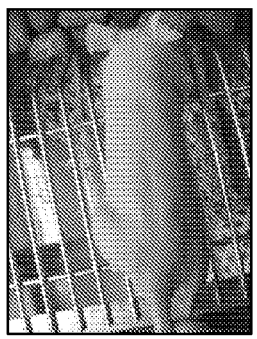 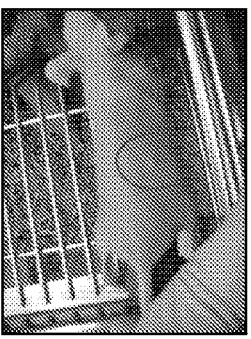 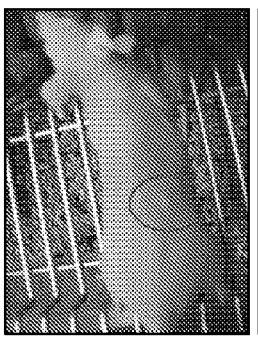 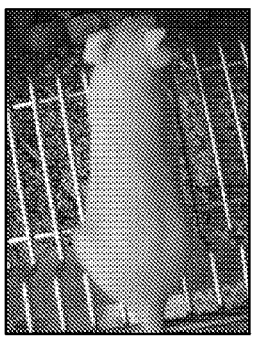
FIG. 7A   FIG. 7B   FIG. 7C   FIG. 7D
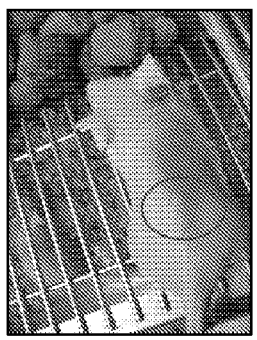 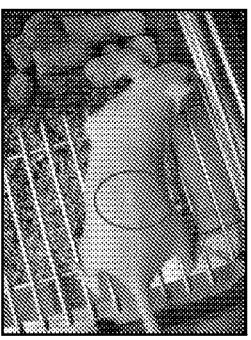 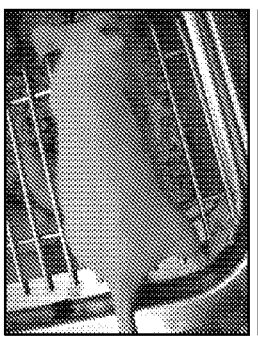 
FIG. 8A   FIG. 8B   FIG. 8C   FIG. 8D

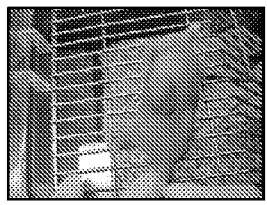 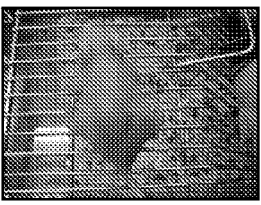 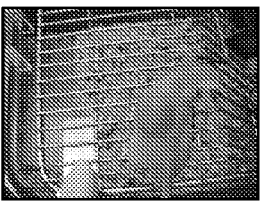 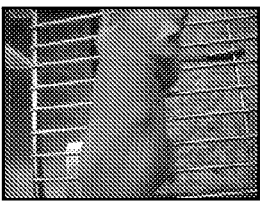
FIG. 10A   FIG. 10B   FIG. 10C   FIG. 10D
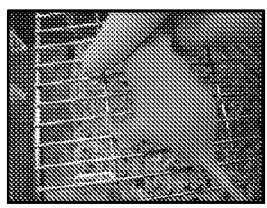 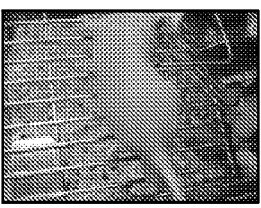 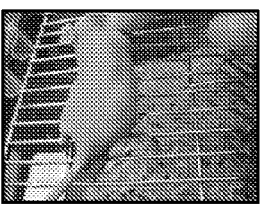 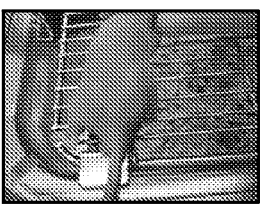
FIG. 11A   FIG. 11B   FIG. 11C   FIG. 11D
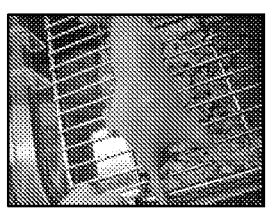 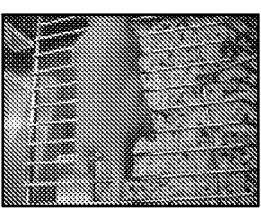 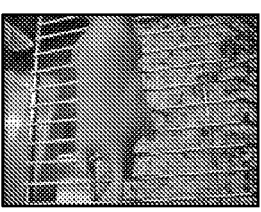 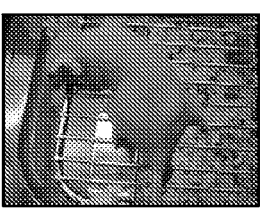
FIG. 12A   FIG. 12B   FIG. 12C   FIG. 12D

METHOD FOR TREATING PROSTATE CANCER

BACKGROUND OF THE INVENTION

It is known that certain naturally occurring non-nutritive agents present in plants and which can be extracted from the plants or fruits may exhibit medical therapeutic properties. In particular, it has been shown that certain flavonoid compounds isolated from citrus juice or from orange peel in the form of a residue extract have been used as a treatment and preventative agent for cancer. See U.S. Pat. No. 7,201,928B1, the entirety of which incorporated herein by reference.

In particular, this patent discloses that orange peel extracts obtained from the cold-press orange peel oil solids waste product from the orange juice industry when tested as an in vivo model in mice, indicated potential efficacy in the treatment of colon cancer. These waste peel oil solids were dissolved in warm ethanol and after repeated washing is used as the medical ingredient for the testing.

SUMMARY OF THE INVENTION

I have discovered that a composition prepared from the rice wine extract of several different species of citrus peels and aloe exhibits significant medicinal properties and is efficacious in the treatment and alleviation of prostate cancer in humans. More specifically, I have discovered that the specific composition utilized in the present inventive method can reduce and place into remission, prostate cancer in humans.

The method of the present invention comprises the treatment of prostate cancer in a human comprising administering to a human in need of such treatment or exhibiting signs of prostate cancer, an anti-prostate cancer effective amount of an extract obtained from fresh citrus peels and aloe. Specifically, the present invention provides a method to inhibit the growth of prostate cancer in a human in need of such treatment by administering an anti-prostate cancer effective amount of a rice wine extract of fresh citrus fruit peels (CPE)

BRIEF DESCRIPTION OF THE DRAWINGS

FIGS. 6A, B, C, and D are photos of untreated mice injected with PC-3 cells;

FIGS. 7A, B, C and D are photos of mice taken 17 days after initiating oral administration with 100 µL of CPE;

FIGS. 8A, B, C and D are photos of mice taken 17 days after initiating oral administration with 200 µL of CPE;

FIGS. 10A, B, C, and D are photos of untreated mice injected with PC-3 cells;

FIGS. 11A, B, C and D are photos of mice taken 21 days after initiating oral administration with 50 µL of CPE;

FIGS. 12A, B, C and D are photos of mice taken 21 days after initiating oral administration with 100 µL of CPE;

DETAILED DESCRIPTION OF THE INVENTION

Figure 1A:
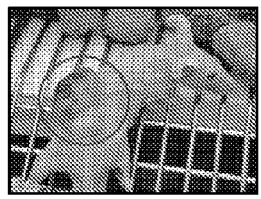
FIGS. 1A, B, C, and D are photos of untreated mice injected with PC-3 cells.
Figure 1B:
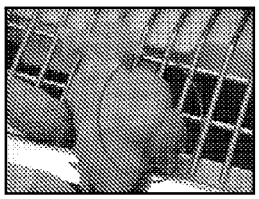
Figure 1C:
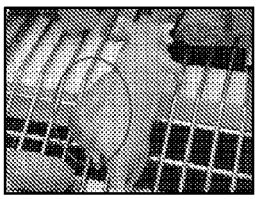
Figure 1D:
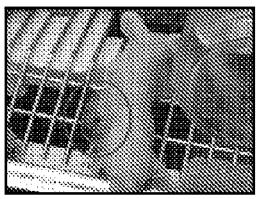
Figure 2A:
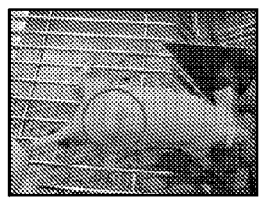
FIGS. 2A, B, C and D are photos of mice taken 18 days after initiating injection with 25 µL of CPE.
Figure 2B:
Figure 2C:
Figure 2D:
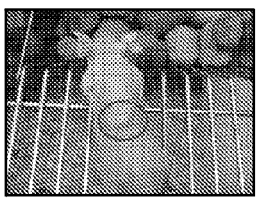

The composition of the present invention may be administered orally, intramuscularly or subcutaneously. The preferable method of administration is oral. Usually, the total daily oral dosage to a human is from about 5 to 120 cc per day, preferably 10 to 60 per day and most preferable 10 to 30 cc per day. This total dosage may be given in one to three daily increments, for example, a total dosage of 10 cc per day might be given in three increments of 3 cc twice-daily and 4 cc once daily. If the total daily dosage is 30 cc, it may be given in three 10 cc increments or one 20 cc dose and one 10 cc dose. The treatment is normally continued until the patient's prostate cancer is in remission, usually as determined by the measurement of the level of protein-specific antigen (PSA) in the blood or other conventional medical procedure for the diagnosis of the presence of prostate cancer. One of skill in the art can use the results of experiments in animals and humans described herein to determine effective amounts to be administered to humans in need of treatment for prostate cancer. By "effective amount" it is meant a concentration that inhibits prostate tumor growth either in vivo in animals or in humans. For example, human test doses can be extrapolated from effective doses in animal studies, such as IC50 values, or from effective doses in vivo by extrapolating on a body weight or surface area basis, e.g., AUC or Area Under the Curve. Such extrapolations are routine in the art. Compositions comprising fresh citrus peel extracts in accordance with the invention can be formulated for administration as a food supplement using one or more fillers.

Nutraceutical compositions can be formulated for administration by any route including, but not limited to, inhalation or insufflation (through mouth or nose), oral, buccal, parenteral, vaginal, or rectal administration. In one embodiment, oral administration, the composition may be added directly to foods and ingested as part of a normal meal. Various methods are known to those skilled in the art for addition or incorporation of nutraceuticals into foods. The inventive composition may be used in concentrations of from 1 to 99 weight percent in a nutraceutical or dietary supplement.

Compositions for use in the present invention can also be administered in the form or tablets or capsules prepared by conventional means with pharmaceutically acceptable excipients such as binding agents, fillers, lubricants, disintegrants, or wetting agents. Examples of specific compounds for use in formulating tablets and capsules are described in detail in the U.S. Pharmacopeia. Tablets comprising the extract can also be coated by methods well known in the art to augment or sustain the activity of the medicament.

Liquid preparations for oral administration can also be used. Liquid preparations can be in the form of solutions, syrups or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives. Again, specific additives are well known to those of skill in the art and are listed in places such as the U.S. Pharmacopeia. In one embodiment, the oral preparation is formulated to provide controlled time release of the active nutraceutical components. For buccal administration the extract can be formulated as a tablet or lozenge.

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose.

Parenterally administered compositions are formulated to allow for injection, either as a bolus or as a continuous infusion. Formulations for injection can be prepared in unit dosage forms, such as ampules, or in multi-dose units, with added preservatives. The compositions for injection can be in the form of suspensions, solutions, or emulsions, in either oily or aqueous vehicles. They may also contain formulatory agents such as suspending agents, stabilizing agents, and/or dispersing agents. The active ingredient may also be presented in powder form for reconstitution with a suitable vehicle before use. Specific examples of formulating agents for parenteral injection are found in the U.S. Pharmacopeia. For rectal administration or vaginal administration, compositions for use in of the present invention can be formulated as suppositories, creams, gels, or retention enemas.

For dietary supplements, the extract can be added in concentrations from 5-95% by weight and mixed according to methods routine in the art. Dietary supplements for animals can be prepared in a variety of forms including, but not limited to, liquid, powder, or solid pill forms. However, the preferable mode of treatment is by administering the inventive composition orally.

The composition of the present invention may be prepared by peeling fresh citrus fruit, mixing the peels thus obtained with rice wine for period of time and at a temperature and pressure sufficient to extract a substantial amount of any rice wine soluble compounds in the citrus fruit into the rice wine. Preferably, the temperature of the extraction step is ambient or room temperature and the pressure is atmospheric pressure. However, the temperature and pressure of the extraction step may be varied to suit the individual needs of the processor. Thus higher temperature and/or pressure conditions may be used to vary the extraction rate.

Alternatively, individual fruit may be peeled and the peels therefrom extracted and then the extracts therefrom mixed and further treated as described herein. Preferably, the rice wine used is Japanese sake, most preferably refined sake of the first class. Generally, such sake has an alcohol content of from about 5-20%, preferably, about 15%.

As a general rule, the extraction time ranges from about 1-25 days, preferably, from 5-20 days and most preferably, from 7-8 days. Thereafter, the remaining peels are separated from the liquid extract by filtration and the thus separated extract is aged for period of from about 1-60 months, preferably 6 to 18 months, and most preferably about 12 months. The aging is preferably carried out at room or ambient temperature. However, this may also be varied, e.g., a higher temperature may be used to suit the specific needs of the processor. The liquid may then be used as is or filtered to remove any solid residue. The alcohol in the composition is not removed but the liquid may be used as is with or without the filtration step in the manner described herein.

I have further discovered that while a variety of citrus species may be used in preparation of the present invention, it is particularly preferable that the peels from the following citrus fruits be used:
navel oranges,
c. hassaku hort (*C. hassaku* hort/*C. hassaku* HORT),
lemon,
*C. aurantium,*
*C. Miyauchi* iyo Hort.,
*C. unshiu,*
fortunella (kumquat/Cumquat), and
*Mikan unsyu* (tangerine).

The peels from these specific fruits may be used individually or in a mixture of the various species. The extract may also contain as an additive, aloe arborescens.

It is further preferable that the citrus fruit peels are obtained from citrus fruit grown and harvested in Japan. Prior to peeling, the citrus fruit is washed with water and is hand-peeled.

A suitable method for preparation of a composition for use in the present invention including appropriate citrus fruit to use is described in U.S. Pat. No. 5,152,990, the entirety of which is hereby incorporated herein by reference.

EXAMPLES

Example 1

The patient was an 80 year old male diagnosed with a urination problem and prostate cancer. The patient refused extirpation of the prostate. The patient was treated orally with the inventive citrus peel extract composition (CPE) for a period of approximately one year. The oral dosage rate was 5 cc, morning, noon and before bedtime for a total dosage of 15 cc per day. The patient also received the following medications during the period: LH-RH (luteinizing hormone-releasing agent by analog injection, naftopidil diuretic and bicalutamide) from Jun. 9, 2004 to Jun. 6, 2005. The patient's PSA was measured on an approximately monthly basis for the year during the treatment period. The results of this treatment and PSA testing are set forth In Table I.

TABLE I

| Date | PSA |
|---|---|
| Jun. 9, 2004 | 278 |
| Jul. 26, 2004 | 19.9 |
| Aug. 23, 2004 | 12.4 |
| Sep. 18, 2004 | 10 |
| Oct. 18, 2004 | 8.95 |
| Nov. 15, 2004 | 7.91 |
| Dec. 13, 2004 | 5.26 |
| Jan. 8, 2005 | 3.89 |
| Mar. 7, 2005 | 1.9 |
| May 9, 2005 | 1.26 |
| Jun. 6, 2005 | 1 |

Example 2

The patient was a 67-year-old male. The patient has had an aorta coronary bypass in 1994, and presented on Jun. 2, 2005, with urination problems. The patient was on the following medications: carvedilol; Bayaspirin; ditiazem hydrochloride and mexiletin hydrochloride. Oral administration of the inventive composition (CPE) was initiated on Jun. 7, 2005 and was continued until Mar. 17, 2007. The initial oral dosage rate was 5 cc in the morning and 5 cc at bedtime for a total of 10 cc per day. The patient's PSA was measured at periodic intervals from Jun. 6, 2005 through Mar. 17, 2007. The results of the treatment and PSA testing are set forth in Table II.

TABLE II

| Date | PSA |
|---|---|
| Jun. 6, 2005 | 24.4 |
| Jun. 22, 2005 | 24.4 |

TABLE II-continued

| | |
|---|---|
| Jul. 14, 2005 | 24.4 |
| Dosage increased to 15 cc (5 cc three times per day) per day on Jul. 2, 2005 | |
| Aug. 2, 2005 | 20.5 |
| Aug. 15, 2005 | 13.3 |
| Aug. 22, 2005* | 13.3 |
| Sep. 21, 2005 | 1.1 |
| Oct. 18, 2005 | 0.5 |
| Dec. 20, 2005 | 0.5 |
| Feb. 14, 2006 | 0.4 |
| Apr. 11, 2006 | 0.4 |
| Aug. 4, 2006 | 0.3 |
| Dec. 4, 2006 | 0.3 |
| Apr. 4, 2007 | 0.3 |

*Patient diagnosed with invasive carcinoma T3aNOMO stage C: Treated with bicalutamide (80 mg); goserelin acetate (3.6 mg) once in 4 weeks injection; tamsulosin hydrochloride diurectic.

The foregoing clinical results show that oral administration of the composition of the present invention to human patients diagnosed with prostate cancer resulted in substantial improvement and mediation of the cancer as evidenced by significant decreases in the PSA measurements over an extended period of time.

Example 3

The therapeutic efficacy of the inventive composition was evaluated in vivo by treating SCID mice bearing human cancer cell tumor xenografts. Specifically, male nude mice (5-wk-old) (purchased from Tzu Chi University Animal Center, Hualien, ROC) were maintained in pathogen-free sterile isolators according to institutional guidelines, and all food, water, caging, and bedding were sterilized prior to use. All procedures were approved by the Japanese National Animal Care and Use Committee of Taiwan. Cancer cells ($5 \times 10^6$) in 0.2 mL phosphate buffered saline (PBS) were injected subcutaneously between the scapulae of each nude mouse. After transplantation, tumor size was measured using calipers and the tumor volume was estimated according to the following formula: tumor volume $(mm^3)=L \times W^2/2$, where L is the length and W is the width. Once tumors reached a mean size of 50-100 $mm^3$, animals received either 50 µl intra-peritoneal injections of PBS (control group), or CPE (low dose: 25 µl and high dose: 50 µl) five times per week for 23 days. Average tumor volume and tumor/body weight ratio of each group were measured at the end of experiment and represent the mean±SD.

Figure 3A:
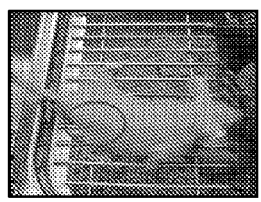
FIGS. 3A, B, C and D are photos of mice taken 18 days after initiating injection with 50 µL of CPE.
Figure 3B:
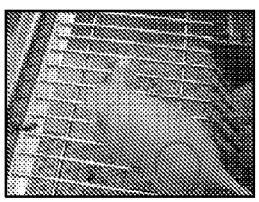
Figure 3C:
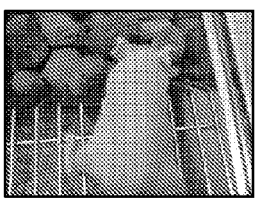
Figure 3D:
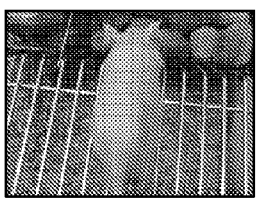

FIGS. 1A, B, C, and D, are photos of untreated mice injected with PC-3 cells. The photos were taken 18 days after the tumor volume reached approximately 50-100 $mm^3$ in size. FIGS. 2 A B, C, and D are photos of mice taken 18 days after initiating injection with 25 µL of CPE five times per week. FIGS. 3A, B, C and D are photos of mice taken 18 days after initiating injection with 50 µL of CPE five times per week. In these photos, the tumors present on each animal are encircled for easier identification.

As can be seen from these figures, the mice treated with 25 µL of CPE showed strong reductions in the PC-3 xenograftic tumor. Those treated with 50 µL of CPE exhibited almost complete reduction in tumor size.

Figure 4:
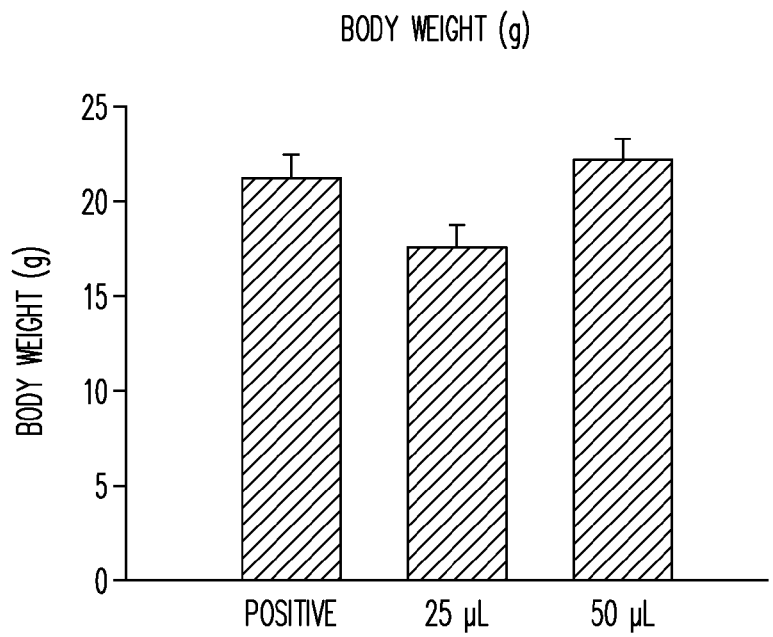
FIG. 4 is a graph showing the variation in body weight of mice after 23 days of treatment.

FIG. 4 is a graph showing the variation in body weight in grams for the three groups of mice described above 23 days after having been treated with injections of CPE or not as in the case with the control group. It can be seen that there was relatively little change in average body weight despite tumor growth.

Figure 5:
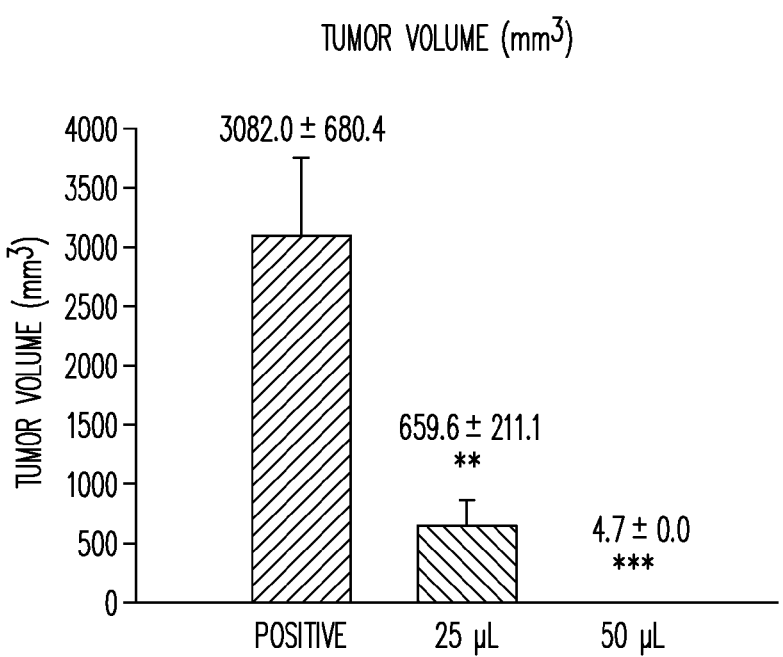
FIG. 5 is a graph showing the variation in tumor volume for mice after 23 days of treatment.

FIG. 5 is a graph showing the variation in tumor volume in $mm^3$ for the three groups of mice described above 23 days after having been treated with injections of CPE or not as in the case with the control group. As shown, a significant reduction in tumor volume was observed between the untreated group and those receiving 25 µL of injection. The reduction in tumor size for those being treated with 50 µL was even much greater (the tumors almost completely disappeared).

Example 4

Three groups of four mice each were treated using the identical injection, components and measurement procedures set forth in Example 3. Once tumors reached a mean size of 50-100 $mm^3$, animals received either 50 µl injections of PBS (control group), or were orally administered CPE in doses of 100 or 200 µL five times per week for 21 days. Average tumor volume and tumor/body weight ratio of each group were measured at the end of experiment and represent the mean±SD.

FIGS. 6A, B, C, and D, are photos of untreated mice injected with PC-3 cells. The photos were taken 17 days after the tumor volume reached approximately 50-100 $mm^3$ in size. FIGS. 7 A B, C, and D are photos of mice taken 17 days after oral administration of 100 µL of CPE five times per week. FIGS. 8A, B, C and D are photos of mice taken 17 days after oral administration of 200 µL of CPE five times per week. In these photos, the tumors present on each animal are encircled for easier identification.

As can be seen from these figures, the mice treated with 100 µL of CPE by oral administration showed strong reductions in the PC-3 xenograftic tumor. Those treated with 200 µL of CPE exhibited even greater reduction in tumor size. Some of the tumors disappeared with the administration of 200 µL.

Example 5

The therapeutic efficacy of CPE was examined in vivo by treating SCID mice bearing human cancer cell tumor xenografts. Male nude mice (5-wk-old) (purchased from Tzu Chi University Animal Center, Hualien, ROC) were maintained in pathogen-free sterile isolators according to institutional guidelines, and all food, water, caging, and bedding were sterilized prior to use. All procedures were approved by the National Animal Care and Use Committee.

Cancer cells ($5 \times 10^6$) in 0.2 mL PBS were injected subcutaneously between the scapulae of each nude mouse. After transplantation, tumor size was measured using calipers and the tumor volume was estimated according to the following formula:

$$\text{tumor volume}(mm^3) = L \times W^2/2, \text{where } L \text{ is the length and } W \text{ is the width.}$$

Once tumors reached a mean size of 50-100 $mm^a$, animals were subjected to intra-peritoneal (i.p.) treatment or oral administration of CPE. For i.p. treatment of CPE, animals received either 50 µL injections of PBS (control group), or CPE (low dose: 25 µL and high dose: 50 µL), five times per week for 23 days. For oral administration of CPE, animals were orally given with either 200 µL of sterile water (control group), or CPE (low dose: 50 µL and high dose: 100 µL). All treatments were given 5 days a week for 21 days. At the end of the experiment, tumors were excised and weighed, and a part of the tumor was fixed in buffered formalin and the remaining portion subjected to western blot analysis. The average tumor volume and tumor/body weight ratio of each group were measured at the end of the experiment and represent the mean±SD.

Results

Anti-Cancer Effects (Xenograft Model)

Figure 9:
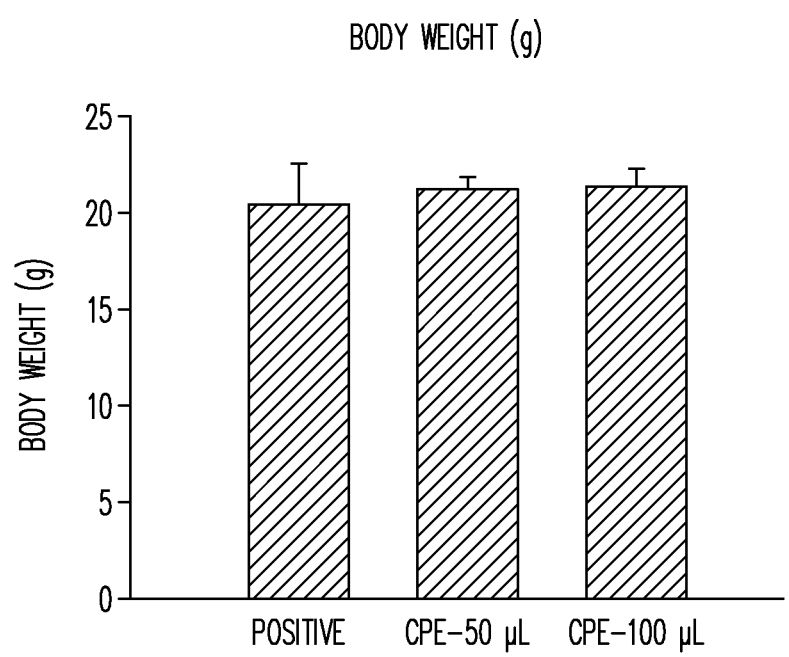
FIG. 9 is a graph showing the variation in body weight of mice after 21 days of treatment.

Oral Administration of CPE Inhibits Tumor Growth In Vivo: The therapeutic efficacy of oral CPE in vivo was examined by treating immunodeficient mice bearing human prostate cancer cell line PC-3 tumor xenografts. Animals received oral administration of 50 and 100 μL CPE five times per week for 21 days. As shown in FIG. 9, the body weight in each group did not show a significant difference (positive group: 20.41±2.11 g, CPE-50 μL 21.22±0.53 g, CPE 100 μL 21.34±0.90 g) and no unhealthy symptoms being observed throughout the study. This suggests that there is no noticeable side effect or toxicity caused by oral administration of CPE. FIGS. 10, A, B, C, and D, are photos of untreated mice injected with PC-3 cells taken 21 days after the tumor volume reached approximately 50-100 mm$^3$ in size. FIGS. 11A B, C, and D are photos of injected mice taken 21 days after initiating oral administration with 50 μL of CPE five times per week. FIGS. 12 A, B, C and D are photos of mice taken 21 days after initiating oral administration with 100 μL of CPE five times per week. In each instance, oral administration of CPE began after the tumor volume reached approximately 50-100 mm$^3$ in size. These photographs clearly show the reduced tumor size in those animals treated in accordance with the present invention.

Figure 13:
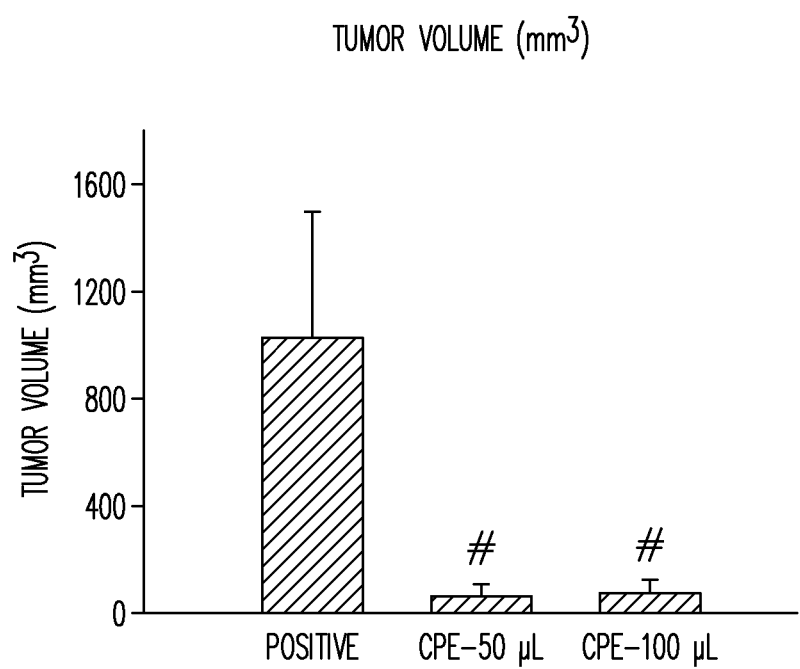
FIG. 13 is a graph showing the variation in tumor volume for mice after 21 days of treatment.

FIG. 13 is a graph depicting the reduction in tumor volume for the mice after 21 days of oral administration with CPE. In particular, we found the average tumor size in the positive (untreated) group was 1021.9±476.2 mm$^3$ which was dramatically reduced in the oral CPE 50 μL and 100 μL groups which each exhibited a volume of 57.7±42.0 mm$^3$. However, no dose response difference was observed between the oral CPE-50 μL and CPE-100 μL group. These results clearly show the increased anti-prostate cancer efficacy of in vivo of the oral administration of CPE.

What is claimed is:

1. A method for the treatment of prostate cancer in a human subject comprising administering to a subject in need of such treatment an anti-prostate cancer effective amount of a rice wine extract of fresh citrus fruit peels.

2. The method of claim 1 wherein the extract is administered orally.

3. The method of claim 1 wherein the extract is administered orally in a dosage amount of from about 5 to 120 ml for 1 to 5 times a day.

4. The method of claim 1 wherein the extract is administered orally in a total daily dosage amount of from 10 to 60 ml.

5. The method of claim 1 wherein the extract is administered orally for a period of time sufficient to cause remission of prostate cancer in the subject.

6. The method of claim 1 wherein the extract is obtained by peeling fresh citrus fruit, mixing the peels thus obtained with rice wine and allowing the mixture to stand for a period of time and at temperature and pressure conditions sufficient to extract substantially all of any rice wine-soluble compounds in the citrus peels into the rice wine.

7. The method of claim 6 wherein the temperature is ambient temperature.

8. The method of claim 6 wherein the temperature is room temperature.

9. The method of claim 6 wherein more than one species of fresh citrus Fruit peels are mixed with the rice wine.

10. The method of claim 9 wherein the fresh citrus peels are obtained from the citrus fruit grown and harvested in Japan.

11. The method of claim 6 wherein the citrus fruit is washed with water prior to peeling.

12. The method of claim 1 wherein the fresh citrus fruit is peeled by hand.

13. The method of claim 9 wherein the fresh citrus fruit is selected from the group consisting of navel oranges, *C. hassaku* hort., lemon. *C. aurantium, C. Miyauchi* iyo Hort., *C. unshiu*, fortunella, tangerine and mixtures thereof.

14. The method of claim 9 wherein the extract further contains aloe arborescens.

15. The method claim 6 wherein the extract is aged at ambient temperature.

16. A method for the therapeutic treatment of a human having prostate cancer comprising administering to the human an anti-prostate cancer effective amount of a rice wine extract of peels from fresh citrus fruit selected from the group consisting of navel oranges. *C. hassaku* hort., lemons. *C. aurantium, C. Miyauchi* iyo Hort., *C. unshiu*, and mixtures thereof.

17. The method of claim 16 wherein the treatment is continued for a period of time sufficient to cause remission of the prostate cancer.

18. The method of claim 16 wherein the treatment is carried by oral administration of the rice wine extract at a dosage amount of 10 ml, two to three times per day.

* * * * *